(12) United States Patent
Rangwala et al.

(10) Patent No.: US 11,583,283 B2
(45) Date of Patent: Feb. 21, 2023

(54) MEDICAL DEVICE WITH ENHANCED SHAPE CHARACTERISTICS

(71) Applicant: MicroVention, Inc., Aliso Viejo, CA (US)

(72) Inventors: Hussain S. Rangwala, Villa Park, CA (US); Ronak Dholakia, Los Angeles, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 139 days.

(21) Appl. No.: 16/931,205

(22) Filed: Jul. 16, 2020

(65) Prior Publication Data

US 2021/0015490 A1 Jan. 21, 2021

Related U.S. Application Data

(60) Provisional application No. 62/874,846, filed on Jul. 16, 2019.

(51) Int. Cl.
*A61B 17/12* (2006.01)
*A61F 2/88* (2006.01)
*A61F 2/90* (2013.01)

(52) U.S. Cl.
CPC .. *A61B 17/12118* (2013.01); *A61B 17/12145* (2013.01); *A61B 17/12172* (2013.01); *A61F 2/88* (2013.01); *A61F 2/90* (2013.01); *A61B 2017/1205* (2013.01); *A61B 2017/12068* (2013.01); *A61F 2210/0014* (2013.01); *A61F 2250/0098* (2013.01)

(58) Field of Classification Search
CPC ........ A61B 17/12118; A61B 17/12145; A61B 17/12172; A61B 2017/00526; A61B 17/12113; A61F 2/88; A61F 2/90; A61F 2002/823; A61F 2/86
See application file for complete search history.

(56) References Cited

U.S. PATENT DOCUMENTS

| 3,868,956 | A | * | 3/1975 | Alfidi | A61F 2/95 606/198 |
| 5,851,206 | A | * | 12/1998 | Guglielmi | A61B 18/082 606/41 |
| 6,063,111 | A | * | 5/2000 | Hieshima | A61B 17/1214 623/1.22 |
| 2004/0034405 | A1 | | 2/2004 | Dickson | |

(Continued)

FOREIGN PATENT DOCUMENTS

| KR | 20200024430 A | 3/2020 |
| WO | WO2016200103 A1 | 12/2016 |

OTHER PUBLICATIONS

WIPO, U.S. International Search Authority, International Search Report and Written Opinion dated Nov. 23, 2020 in International Patent Application No. PCT/US2020/042377, 13 pages.

*Primary Examiner* — Katherine H Schwiker
*Assistant Examiner* — Serenity A Miller
(74) *Attorney, Agent, or Firm* — Inskeep IP Group, Inc.

(57) ABSTRACT

A medical device is disclosed and may have a spiral shape structure that can function as a stent, such as a flow diversion stent to treat aneurysms. The medical device may have a spiral shape structure that can function as an occlusive device, for instance to occlude aneurysms. The medical device may include a shape setting structure to selectively adjust the shape of the medical device.

17 Claims, 10 Drawing Sheets

(56) References Cited

U.S. PATENT DOCUMENTS

| | | |
|---|---|---|
| 2007/0244550 A1 | 10/2007 | Eidenschink |
| 2007/0265631 A1 | 11/2007 | Fox |
| 2010/0094335 A1 | 4/2010 | Gerberding et al. |
| 2010/0268204 A1* | 10/2010 | Tieu ................. A61B 90/39 606/108 |
| 2014/0058436 A1* | 2/2014 | Rosenbluth ...... A61B 17/12172 606/200 |
| 2015/0134044 A1 | 5/2015 | Kim et al. |
| 2019/0003024 A1 | 1/2019 | Elliot |
| 2019/0239895 A1* | 8/2019 | Dawson ................. A61F 2/962 |

* cited by examiner

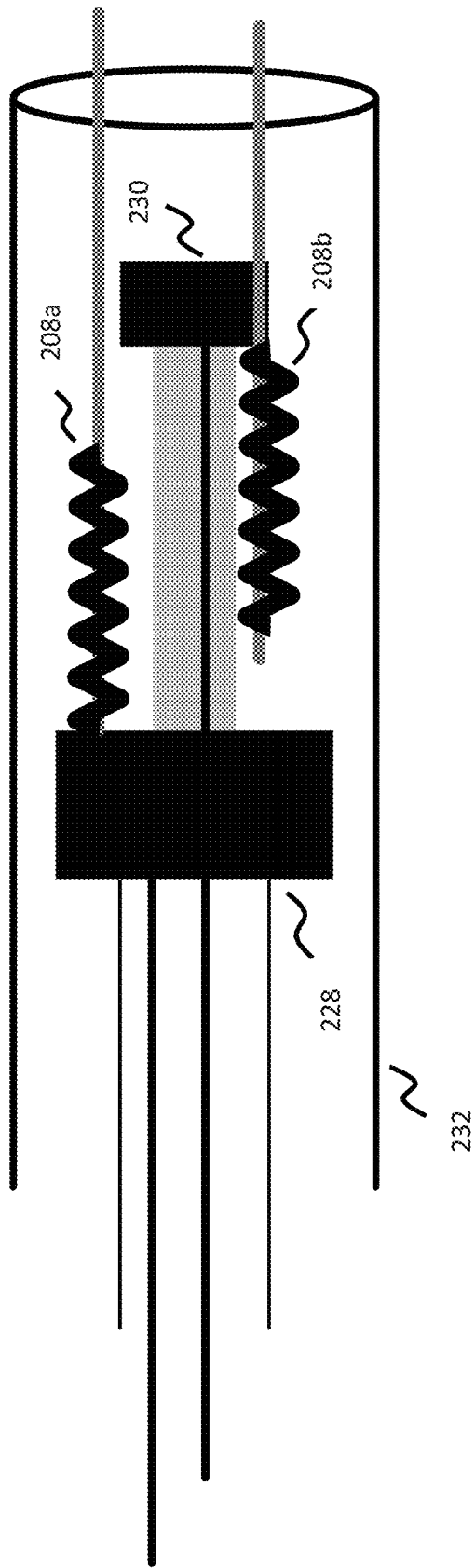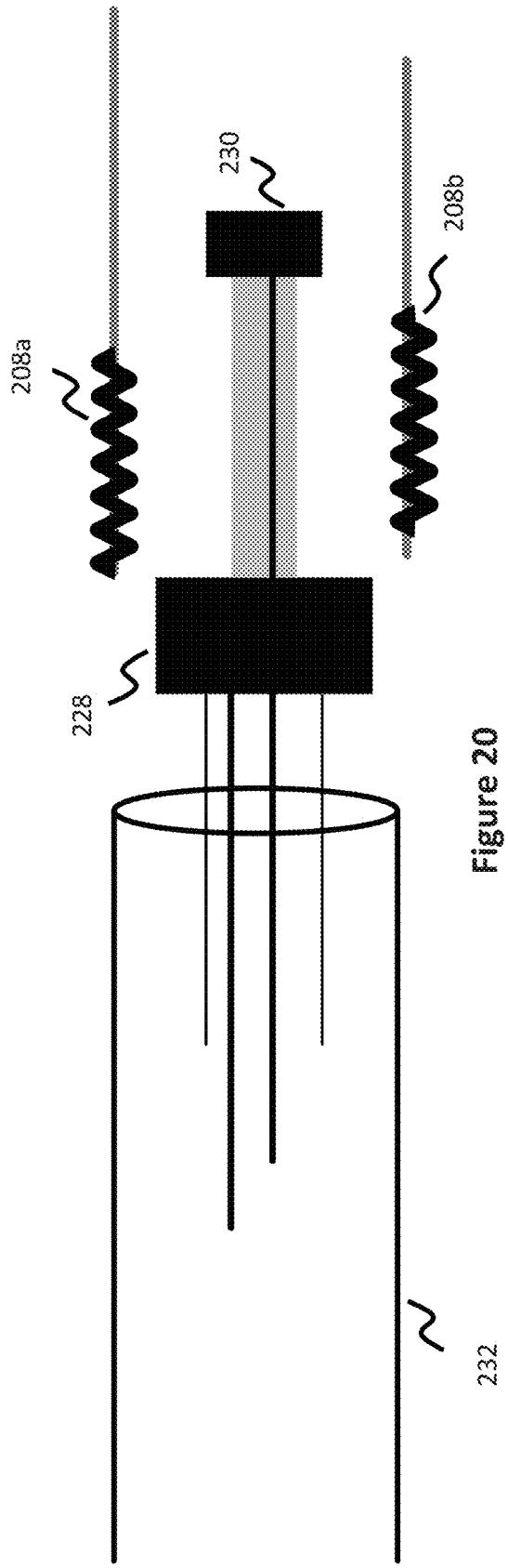
Figure 19
Figure 20

MEDICAL DEVICE WITH ENHANCED SHAPE CHARACTERISTICS

RELATED APPLICATIONS

This application is the nonprovisional of and claims priority to U.S. Provisional Application Ser. No. 62/874,846 filed Jul. 16, 2019 entitled Spiral Flow Diverter, which is hereby incorporated herein by reference in its entirety.

BACKGROUND OF THE INVENTION

Aneurysms are bulges along a blood vessel wall caused by, for example, a weakening of an arterial region. Left untreated, aneurysms can rupture over time leading to complications such as stroke. Intracranial aneurysm rupture translates into hemorrhagic stroke that either proves fatal or results in permanent neurological impairment in patients.

Aneurysms are traditionally treated utilizing clipping or occlusion. Occlusion involves filling the aneurysm with an occlusive device, such as coils, to occlude flow to the aneurysm and cut off blood supply to the aneurysm over time.

Recent techniques in aneurysm treatment have utilized the use of flow diversion stents, which are braided tubular devices placed across the neck of an aneurysm. The flow diversion stents (also known as flow diverters) utilize a low porosity interface to limit blood flow into the aneurysm, inducing flow stagnation within the aneurysm and thereby helping cut off blood supply into the aneurysm over time to reduce the probability of rupture and encouraging endothelial growth over the stent to seal off the aneurysm over time.

Traditional flow diverters utilize a fixed tubular or cylindrical stent structure with a consistent low porosity profile over an entire length of the stent. However, this design can cause complications. For instance, due to its fixed tubular shape, the typical flow diversion stent is stiff, making deployment troublesome in particular circumstances—such as a scenario where an aneurysm is located along a tortuous section of the anatomy. Furthermore, traditional flow diversion stents are not repositionable after a certain point during the deployment process. Typically, there is a mechanical linkage between a delivery pusher and the stent, and once the stent loses engagement with this linkage (e.g., when the stent expands upon delivery), the stent is no longer connected to the delivery pusher and can no longer be repositioned.

Traditional flow diverters have a fixed size, where a physician would need to size a blood vessel prior to a procedure and then utilize a particularly sized flow diverter to fit the particular target location. Complications can result if the stent does not properly expand (e.g., due to pressure from the vessel wall, or deployment across a tortuous bend) or if the stent is incorrectly sized causing complications with the flow diversion characteristics of the stent. For instance, if the stent is too small then the stent may not sit flush across the neck of the aneurysm thereby hindering the flow diversion effect of the stent. If the stent is too large relative to the vessel, then the stent may not deploy properly from the delivery catheter or assume the correct shape after deployment.

There is a need for a flow diverting stent that addresses at least these issues.

In certain scenarios, occlusion, rather than flow diversion, may be deemed a better treatment option to treat aneurysms. A newer class of occlusion devices are known as intrasaccular devices and tend to focus on flow disruption at the neck of an aneurysm to help prevent blood flow into the aneurysm. These intrasaccular devices utilize a structure such as a mesh to occupy the space within the aneurysm to provide occlusion and prevent blood flow into the aneurysm, while also providing a barrier along the neck of the aneurysm. Often, these devices are highly conformable to adjust to the size and dimensions of the aneurysm. However, it can be difficult to design an intrasaccular device that sufficiently occludes an aneurysm while also enabling good coverage of the neck of the aneurysm, to help prevent blood flow into the aneurysm. Generally, this is since the occlusion device (including an intrasaccular device) has a fixed shape and structure.

There is a need for an occlusion device that addresses at least these issues.

Traditional medical devices (e.g., stents or occlusive devices) have a particular fixed size and are often heat set into an expansion state which the device adopts upon deployment from a delivery catheter. Therefore, there is a fixed smaller profile delivery state when the device is within a catheter, and a fixed heat set expanded state when the device is outside of the catheter. However, there is no way to adjust the size or shape of the device after deployment, where the ability of an implant to adopt an alternative shape can help augment treatment of a particular target area.

There is a need for a medical device, such as a stent or occlusion device, that addresses at least these issues.

SUMMARY OF THE INVENTION

In some embodiments, a stent is described.

In one embodiment, a stent with particular utility as a flow diverting stent used in treating aneurysms is described. In one embodiment, a stent utilizes a spiral shape. In one embodiment, a stent is composed of one or more metallic wires braided into a spiral shape. In one embodiment, a stent utilizes a multi-layer (e.g., dual-layer) spiral shape. In one embodiment, a multi-layer stent utilizes wires where some wires in one layer are offset relative to some wires in another layer to thereby augment a flow disruptive effect of the stent.

In one embodiment, a stent utilizes a shape setting structure to adjust the profile of the stent. In one embodiment, a shape setting structure is one or more wires connected to the stent. In one embodiment, a shape setting structure is one or more wires which are inter-braided or interwoven with the stent. In one embodiment, a shape setting structure is a scaffold type structure. In one embodiment, a shape setting structure utilizes conductive elements (e.g., wires). In one embodiment, a shape setting structure undergoes a heat treatment step such that the shape setting structure adopts a particular shape when heated to a particular temperature. In one embodiment, a shape setting structure is heated to a particular temperature to adopt a particular shape, in order to urge an implant into a particular shape. In one embodiment, a stent has particular utility as a flow diverting stent used in treating aneurysms.

In one embodiment, a method of treating a vascular condition with a stent is described. A method comprises providing a stent with a spiral shape, deploying the stent through a delivery catheter and out of a delivery catheter such that the stent adopts its spiral shape, thereby treating a vascular condition with the spiral shaped stent. In one embodiment, a stent is composed of one or more metallic wires braided into a spiral shape. In one embodiment, a stent utilizes a multi-layer (e.g., dual-layer) spiral shape. In one embodiment, a multi-layer stent utilizes wires where some wires in one layer are offset relative to some wires in another layer to thereby augment a flow disruption effect of the stent. In one embodiment, a method of treating an aneurysm is described. A method comprises providing a flow diverter stent with a spiral shape, deploying a flow diverter stent through a delivery catheter and out of a delivery catheter such that the flow diverter stent adopts its spiral shape, thereby impeding blood flow into the aneurysm with the spiral shaped stent.

In one embodiment, a method of treating a vascular condition is described. A method comprises providing a stent, deploying a stent through a delivery catheter and at least partially out of the delivery catheter so that at least a portion of the stent takes on an expanded shape, and activating a shape setting structure to cause the stent to adopt a different shape configuration (e.g., a spiral). In one embodiment, a shape setting structure is one or more wires connected to a stent. In one embodiment, a shape setting structure is one or more wires which are inter-braided or interwoven with a stent. In one embodiment, a shape setting structure is a scaffold type structure. In one embodiment, a shape setting structure utilizes conductive elements (e.g., wires). In one embodiment, a shape setting structure undergoes a heat treatment step such that the shape setting structure adopts a particular shape when heated to a particular temperature. In one embodiment, a shape setting structure is heated to a particular temperature to adopt a particular shape, in order to urge an implant into a particular shape. In one embodiment, a stent has particular utility as a flow diverting stent used in treating aneurysms. In one embodiment, a method of treating an aneurysm is described. A method comprises providing a flow diversion stent, deploying the flow diversion stent through a delivery catheter and at least partially out of the delivery catheter so that at least a portion of the stent takes on an expanded shape, activating a shape setting structure to cause the flow diversion stent to adopt a different shape configuration (e.g., a spiral).

In some embodiments, an occlusive device is described.

In one embodiment, an occlusive device is used to occlude an aneurysm. In one embodiment, an occlusive device utilizes a spiral shape. In one embodiment, an occlusive device is composed of one or more metallic wires braided into a spiral shape. In one embodiment, an occlusive device utilizes a multi-layer (e.g., dual-layer) spiral shape. In one embodiment, a multi-layer occlusive device utilizes wires where some wires in one layer are offset relative to some wires in another layer to thereby augment a resistance to blood flow or flow disruption.

In one embodiment, a method of occluding an aneurysm is described. A method comprises deploying an occlusive device through a delivery catheter and out of the delivery catheter and into an aneurysm, whereby an occlusive device adopts its spiral, expansion shape to occlude the aneurysm. In one embodiment, an occlusive device is composed of one or more metallic wires braided into a spiral shape. In one embodiment, an occlusive device utilizes a multi-layer (e.g., dual-layer) spiral shape. In one embodiment, a multi-layer occlusive device utilizes wires where some wires in one layer are offset relative to some wires in another layer to thereby augment a resistance to blood flow or flow disruption. In one embodiment, a method of occluding a treatment area is described. A method comprises deploying an occlusive device through a delivery catheter and out of the delivery catheter and into the treatment area to treat a vascular condition, whereby the occlusive device adopts its spiral, expansion shape to occlude the treatment area.

In one embodiment, an occlusive device which utilizes a shape setting structure to adjust a shape, configuration, or profile of the device is described. In one embodiment, a shape setting structure is one or more wires connected to an occlusive device. In one embodiment, a shape setting structure is one or more wires which are inter-braided or interwoven with an occlusive device. In one embodiment, a shape setting structure is a scaffold type structure. In one embodiment, a shape setting structure utilizes conductive elements (e.g., wires). In one embodiment, a shape setting structure undergoes a heat treatment step such that the shape setting structure adopts a particular shape when heated to a particular temperature. In one embodiment, a shape setting structure is heated to a particular temperature to adopt a particular shape, in order to urge an implant (e.g., occlusive device) into a particular shape. In one embodiment, an occlusive device has particular utility as an aneurysm occluder, such as an intrasaccular device.

In one embodiment, a method of occluding a treatment area is described. A method comprises delivering an occlusive device through a delivery catheter and out of the delivery catheter so that at least a portion of the occlusive device is outside of the delivery catheter, activating a shape setting structure to adjust a shape, profile, or configuration of the occlusive device, and occluding the treatment area with the occlusive device. In one embodiment, a shape setting structure is one or more wires connected to the occlusive device. In one embodiment, a shape setting structure is one or more wires inter-braided or interwoven along with the occlusive device. In one embodiment, a shape setting structure is a scaffold-type structure. In one embodiment, a shape setting structure utilizes conductive elements (e.g., wires). In one embodiment, a shape setting structure undergoes a heat treatment step such that the shape setting structure adopts a particular shape when heated to a particular temperature. In one embodiment, a shape setting structure is heated to a particular temperature to adopt a particular shape, in order to urge an implant (e.g., occlusive device) into a particular shape. In one embodiment, an occlusive device has particular utility as an aneurysm occluder, such as an intrasaccular device. In one embodiment, a method of occluding an aneurysm is described. A method comprises delivering an occlusive device through a delivery catheter and out of the delivery catheter so that at least a portion of the occlusive device is outside of the delivery catheter and in the aneurysm, activating a shape setting structure to adjust the shape or configuration or profile of the occlusive device, and occluding the aneurysm with the occlusive device.

In one embodiment, a method of manufacturing a medical device, including a flow diverting stent and/or an occlusive device, is described. A method comprises forming a tubular structure, in one embodiment by braiding one or more wires on a mandrel to form a tubular structure composed of one or more layers. A tubular structure is then compressed to form a compressed multiple-layer structure. A multiple-layer structure is then spirally wound around a tubular mandrel in order to create a multiple-layer, spiral tubular shape. In one embodiment, one or more wires at a proximal end of a medical device are releasably connected to a delivery pusher to deliver the medical device.

In one embodiment, a medical device utilizes a mechanical delivery pusher connected to a proximal end of the medical device. In one embodiment, a medical device is a spiral-shaped member. In one embodiment, a medical device is a stent—such as a flow-diversion stent. In one embodiment, a medical device is an occlusive device. In one embodiment, a delivery system utilizes a connection interface between a delivery pusher and a medical device where the connection interface comprises proximally-positioned wires which comprise a proximal portion of the medical device. In one embodiment, a delivery pusher includes a detachment system to detach the delivery pusher from the medical device. In one embodiment, a thermal detachment system is utilized. In one embodiment, a detachment system includes a first system to detach the medical device and a second system to activate a shape setting structure to adjust a shape, profile, or configuration of the medical device.

In one embodiment, a method of detaching a medical device (e.g., stent or occlusive device) is described. A method comprises delivering a medical device to a treatment site (e.g., aneurysm), deploying the medical device, and activating a detachment system to detach a delivery pusher from the medical device.

In one embodiment, a shape setting system including a shape setting structure is described. In one embodiment, a shape setting system utilizes a shape setting structure (in one embodiment, one or more conductive wires), and a heating system connected to the shape setting structure to convey current through and thereby heat the shape setting structure. In one embodiment, heating the shape setting structure adjusts its shape, profile, or configuration (e.g., either causing it to elongate, or causing it to expand, or causing it to adopt a different shape) thereby adjusting or changing a shape, profile, or configuration of a medical device/implant connected to or integral with the shape setting structure. In one embodiment, a shape setting structure utilizes a structure (e.g., one or more wires) which is heat set into a particular shape at a particular transition temperature such that when the structure is later exposed to this transition temperature, it then adopts the heat-set shape. In one embodiment, the medical device is a stent—such as a flow diversion stent. In one embodiment, the medical device is an occlusive device.

In one embodiment, a method of using a shape setting system or shape setting structure to change a shape, profile, or configuration of a medical device or implant (e.g., stent or occlusive device) is described. A method comprises activating a heating system connected to a shape setting structure to convey current through and thereby heat the shape setting structure, thereby adjusting its shape or profile or configuration, and thereby adjusting the shape or profile or configuration of a medical device connected to or integral with the shape setting structure. In one embodiment, a method of creating a shape setting structure comprises winding a shape setting structure over a mandrel into a particular shape, and heat setting the shape at an appropriate transition temperature that is above body temperature in order to impart the transition temperature into the shape setting structure.

In one embodiment, a medical device which can selectively function as either a stent or an occlusive device is described. In a first configuration, a device functions as a flow diversion stent to sit across a neck of an aneurysm to divert blood flow from the aneurysm. In a second configuration, a device functions as an occlusive device placed within an aneurysm to occlude the aneurysm.

In one embodiment, a method of utilizing a medical device which can selectively function as either a stent or an occlusive device is described. A method comprises deploying a medical device to a treatment site (e.g., aneurysm), deploying the medical device out of a delivery catheter to cause the medical device to adopt a different shape, and treating the medical condition with the different shape. In one embodiment, the method further comprises activating a shape setting structure connected to the medical device to cause the medical device to adopt a different shape in order to treat the target site with the medical device having the different shape.

In one embodiment a method of changing a shape of an implantable device is described. A method comprises providing a scaffold having a constrained state, an unconstrained state and a pre-set shape; providing a shape-changing device associated with said scaffold; and selectively activating said shape-changing device to change said scaffold from said unconstrained state to said pre-set shape.

In one embodiment a medical implant is described. A medical implant comprises a tubular structure; the tubular structure configured to have a resting shape and an operative shape; a shape setting mechanism associated with the tubular structure; the shape setting mechanism operative to selectively change the tubular structure from the resting shape to the operative shape.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 19 illustrates the interface of FIG. 18 when within a delivery catheter, according to one embodiment.

FIG. 20 illustrates the interface of FIG. 18 when not within a delivery catheter, according to one embodiment.

DESCRIPTION OF EMBODIMENTS

Stents are used for a variety of reasons in the vasculature, for instance acting as a scaffold to help vessel patency. One class of stents, discussed earlier, are known as flow diversion stents and are implanted in the vessel adjacent the neck of an aneurysm to help reduce or limit blood flow into the aneurysm. Where porosity is defined as the amount of open space in the stent (e.g. the inverse of the percentage of area comprised by the stent material itself), flow diversion stents utilize a relatively low porosity to help limit the amount of blood flow into the aneurysm.

Traditional stents, including flow diversion stents, utilize a fixed tubular structure. However, this design is generally stiff and can therefore cause complications in deployment—for instance in smaller blood vessels (e.g., those in the neurovasculature), or deployment along tortuous anatomy. The following embodiments generally deal with stents, including flow diversion stents, and have particular utility in treating aneurysms in the neurovasculature.

Figure 1:
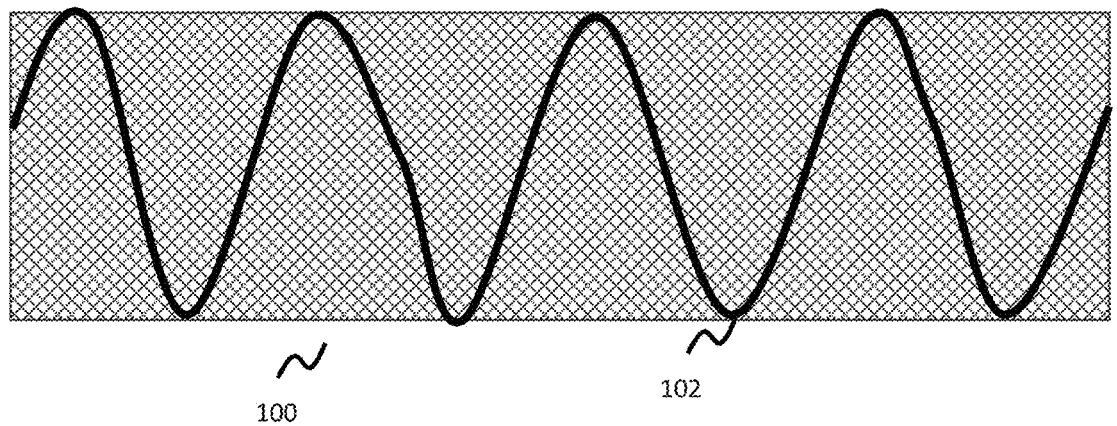
FIG. 1 illustrates a tubular structure used to create a multiple layer implant, according to one embodiment.

FIG. 1 shows a tubular structure 100, used to create a spiral shaped stent. Tubular structure 100 is composed of a mesh or braid of one or more wires, braided together to form this shape. In one embodiment, metallic shape memory wires (e.g., nitinol, stainless steel, cobalt-chromium) are used. In one preferred embodiment, nitinol is used. In one embodiment, drawn-filled tubing (DFT) utilizing a radiopaque (e.g., platinum or tantalum) core and an outer metallic (e.g., nitinol) jacket are used; these DFT elements appear similar to and function similarly to wires.

Tubular mesh or braid 100, in one embodiment, utilizes an optional radiopaque wire 102 (e.g., tantalum or platinum) to aid in visualization. Radiopaque wire 102 is interwoven among the rest of the braid 100, such that radiopaque wire 102 is formed as part of the braid or mesh. In one embodiment, radiopaque wire 102 is wound at the same time and in a similar manner as the other wires of the braid. In one embodiment, radiopaque wire 102 is wound in an over-under manner in relation to the other wires of the braid (e.g., over a wire portion, under another wire portion, etc.) so as to interweave radiopaque wire 102 as part of the mesh. In one embodiment, radiopaque wire 102 is wound subsequent to the other wires of the implant as an additional step, and is wound in an over-under pattern in relation to the other wires of the mesh (e.g., in the over-under manner described above) so as to interweave radiopaque wire 102 as part of the mesh.

In one embodiment, radiopaque/visualization wire 102 is thicker than the wire(s) of the rest of the braid 100. This increased thickness can offer advantages in terms of visualization and in terms of imparting increased stiffness to tubular braid 100 (this is since radiopaque materials are often stiffer than their more pliable shape-memory counterparts). In one example, braid 100 is composed of one or more wires of about 0.01 mm-0.08 mm diameter, while radiopaque wire 102 is about 0.05 mm-0.15 mm in diameter. In one example, braid 100 is composed of one or more wires of about 0.025 mm-0.075 mm diameter, while radiopaque wire 102 is about 0.05 mm-0.1 mm in diameter.

Figure 2:
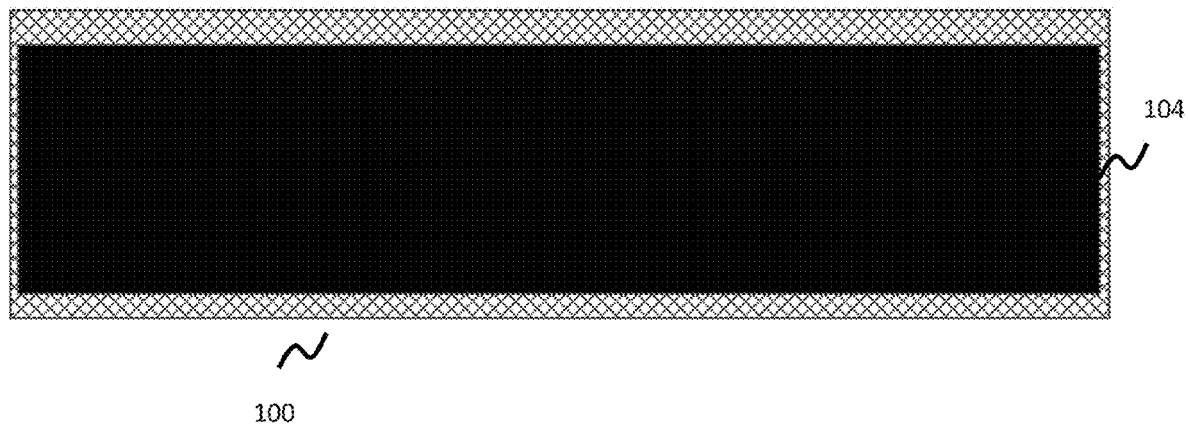
FIG. 2 illustrates the tubular structure of FIG. 1 positioned over a mandrel, according to one embodiment.
Figure 3:
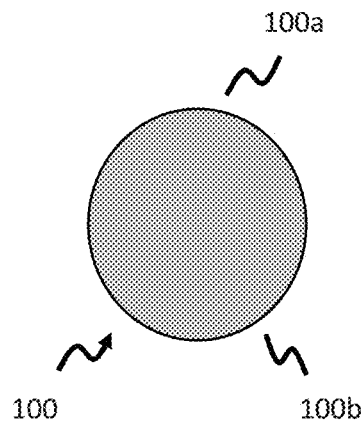
FIG. 3 illustrates a front profile of a tubular structure, according to one embodiment.

In one embodiment, tubular mesh or braid 100 is a single layer and is formed by braiding one or more wires around a tubular mandrel to create a tubular mesh shape—as shown in FIG. 2 with mandrel 104. A general cross-sectional profile of this tubular shape is shown in FIG. 3. This view can be thought of as the front of the tubular shape. In various embodiments, mandrel 104 can either be horizontally or vertically oriented. A horizontal mandrel configuration is shown in FIG. 2. A vertical mandrel configuration would flip the mandrel 90 degrees so that any winding would take in a vertical manner (e.g., either against gravity or with gravity). One advantage to a vertical mandrel configuration is when wound from a top-down manner, gravity can be used as an extra force to aid in the winding process.

Figure 4:
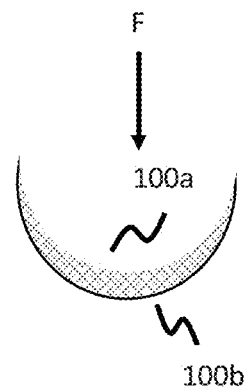
FIG. 4 illustrates a compressed front profile of a tubular structure, according to one embodiment.
Figure 5:
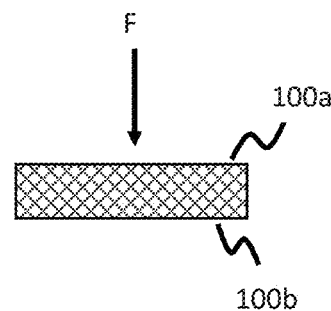
FIG. 5 illustrates a compressed front profile of a tubular structure, according to another embodiment.
Figure 6:
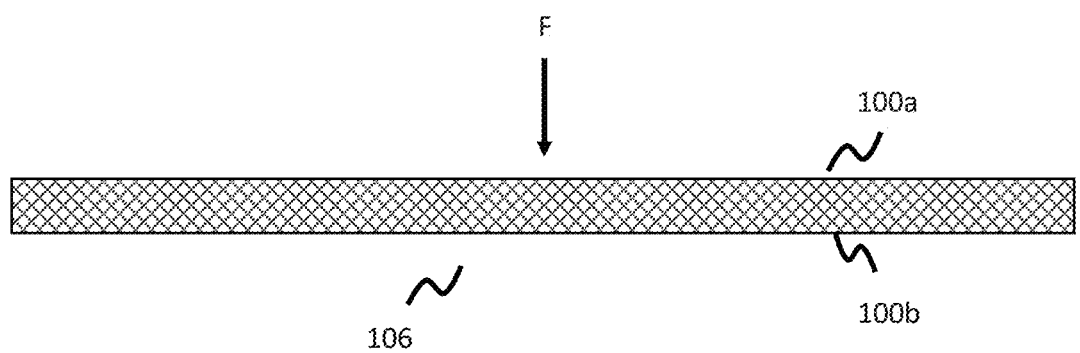
FIG. 6 illustrates a side view of a compressed tubular structure, according to one embodiment.

Following this step, tubular mesh or braid 100 is subsequently configured into a spiral shape. Tubular mesh 100 is first removed from mandrel 104 and compressed in order to create a multiple layer (e.g., dual-layer) structure. This is shown in the context of FIGS. 3-5. In FIG. 3, a tubular shape is created with a top tubular section 100*a* and a bottom tubular section 100*b*. The tubular shape is then compressed (via a Force F) to create a different cross-section shown in either FIG. 4 or FIG. 5. In FIG. 4, the tubular shape is compressed so that top 100*a* and bottom 100*b* tubular sections are adjacent or nearly adjacent, to create a compressed and curved structure. In FIG. 5, the tubular shape is compressed to create a flat cross-sectional shape, which in some embodiments can be thought of as a flat or thin ribbon type of shape. FIG. 6 shows the side view of the originally tubular structure once flattened or compressed to adopt an elongated and compressed shape 106, this can be thought of as the side profile of the tubular structure 100 of FIG. 1 after being flattened or compressed to adopt a different shape 106.

Following this step, tubular mesh or braid 100 is subsequently configured into a spiral shape. Tubular mesh 100 is first removed from mandrel 104 and compressed in order to create a multiple layer (e.g., dual-layer) structure. This is shown in the context of FIGS. 3-5, which represent a frontal view or cross-section of a tubular structure 100 (e.g., if a user were facing a lumen of the tubular structure 100). In FIG. 3, a tubular shape is created with a top tubular section 100*a* and a bottom tubular section 100*b*. The tubular shape is then compressed (via a Force F) to create a different cross-section shown in either FIG. 4 or FIG. 5. In FIG. 4, the tubular shape is compressed so that top 100*a* and bottom 100*b* tubular sections are adjacent or nearly adjacent, to create a compressed and curved structure. In FIG. 5, the tubular shape is compressed to create a flat cross-sectional shape, which in some embodiments can be thought of as a flat or thin ribbon type of shape. FIG. 6 shows the side view of the originally tubular structure once flattened or compressed to adopt an elongated and compressed shape 106, this can be thought of as the side profile of the tubular structure 100 of FIG. 1 after being flattened or compressed to adopt a different shape 106. The view of FIG. 6 also can be considered as the tubular structure of FIGS. 3-5 rotated 90 degrees to show a side instead of frontal view, after being compressed.

Since the spiral shape is created from a two-layer structure composed of a first layer 100*a* positioned over a second layer 100*b*, as shown in FIGS. 4-6, the spiral itself will be two layers. However, in other embodiments, even more layers can be used (e.g., if a multiple layer tubular braid is initially created, then compressing the braid will further multiply these layers). Therefore, the spiral itself will be comprised of at least two layers, but can also be composed of more layers (e.g., 4, 6, 8, 10, or more).

Figure 7:
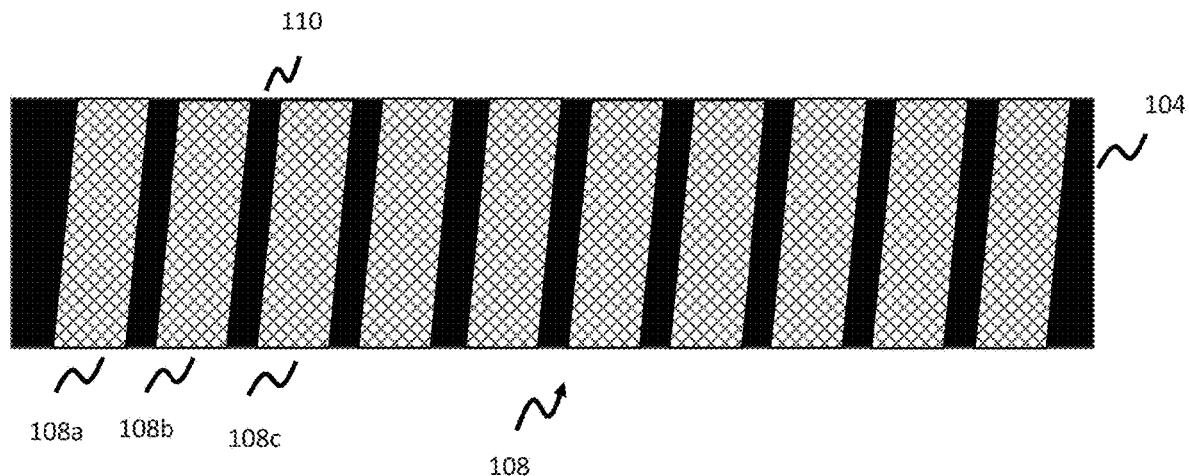
FIG. 7 illustrates a spiral structure positioned over a mandrel, according to one embodiment.
Figure 8:
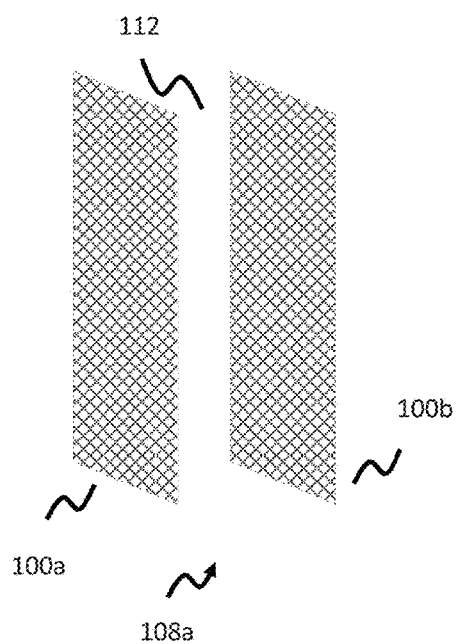
FIG. 8 illustrates a side profile of a spiral structure, according to one embodiment.

A multi-layer spiral configuration is shown in FIG. 8, where an individual or particular spiral component (e.g., one winding 108a of the spiral pattern 108) is composed of two overlapping layers 100a, 100b. Layers 100a, 100b can be configured so that there is an open space or gap 112 between the layers (note this is different than gap 110 of FIG. 7 which denotes the gap between adjacent windings of the spiral pattern 108). Open space or gap 112 can be controlled by utilizing tie elements along particular locations which tie the two layers together, where the number of connections and the binding strength/tension between the layers affect any open space/gap size. Alternatively, an adhesive binding can be used where areas between the adhesive points would be somewhat spaced out to create regions with open spaces/gaps.

Alternatively, layers 100a, 100b can be configured so there is no such open space, such that one layer is directly against another layer in a flush manner. The flush positioning can be achieved, for instance, by utilizing a number of tightly configured tie elements along several sections of each windings of the spiral pattern, or by utilizing a continuous/substantially continuous adhesive section to tightly bind layers 100a, 100b together.

Figure 9:
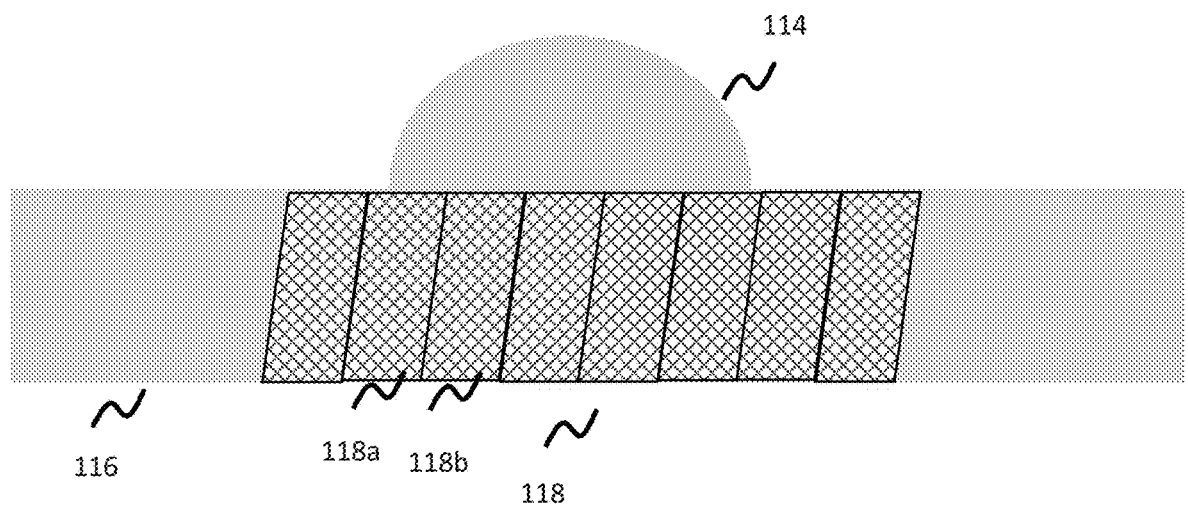
FIG. 9 illustrates a spiral shaped stent treating an aneurysm, according to one embodiment.

A multiple layer spiral pattern (meaning, where each winding of the spiral pattern is composed of two or more layers) has some significant advantages where the spiral pattern shape is used as a stent, and in particular as a flow diversion stent (also known as a flow diverter). This is shown in the context of FIG. 9 where a spiral flow diversion stent 118 is composed of a plurality of individual windings 118a, 118b, etc. where each winding 118a, 118b, etc. is its own individual spiral component. Flow diversion stent 118 is implanted into a blood vessel 116 adjacent an aneurysm 114, and is used to reduce blood blow into the aneurysm and promote clotting at a neck region of the aneurysm to close off the aneurysm.

Figure 10:
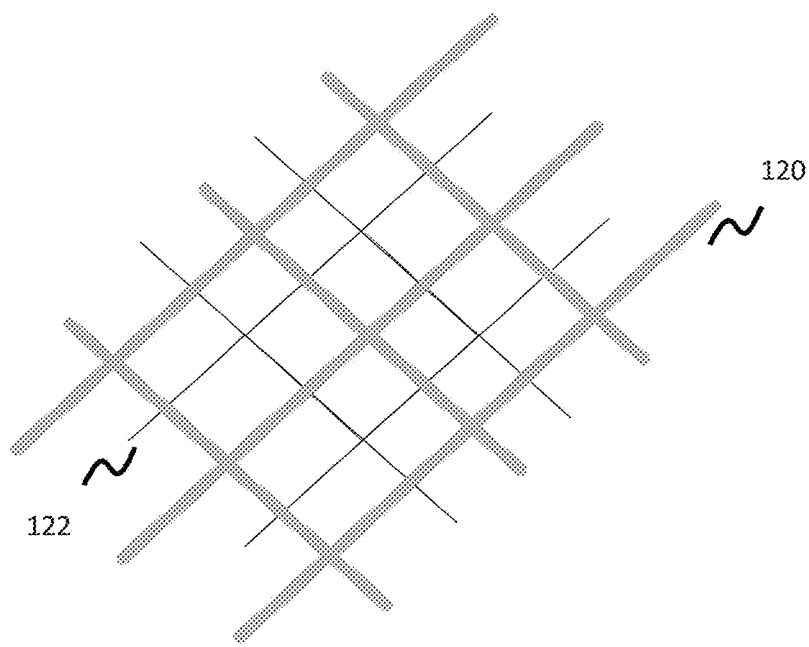
FIG. 10 illustrates multiple wire layers used in a spiral structure, according to one embodiment.

Since each winding 118a, 118b, etc. is composed of multiple (e.g., at least two) layers—as discussed earlier and herein, any blood that passes through the flow diversion stent 118 would need to pass through multiple layers of wires in order to enter the aneurysm, thereby creating a blood flow barrier and resulting in augmented flow disruption or flow diversion. Wires of each layer of the windings of the spiral-shaped stent 118 therefore provide a flow diversion barrier to blood entering the aneurysm where each subsequent layer offers an additional barrier. In one embodiment, a flow diversion effect is further augmented when the wires of one layer are offset relative to wires in another layer. This configuration is shown in FIG. 10 where wires 120 (larger, gray lines) of one layer are offset relative to wires 122 (smaller, black lines) of another layer. Though line/wire sizes are illustratively shown as different in the context of FIG. 10, in one embodiment, the wires of the braid comprising the spiral flow diversion stent are substantially similar. An offset configuration, as can be appreciated from FIG. 10, would augment resistance to blood flow and increased flow diversion. An offset pattern can be configured, for instance, by binding the layers together (e.g., via mechanical ties, welding, or adhesive) in such a manner that one layer is offset relative to another layer.

In another embodiment, the layers are configured such that one layer is not offset relative to another, meaning the wires of one layer are substantially aligned with the wires of another layer. This alignment can be configured, for instance, by binding the layers together (e.g., via mechanical ties, welding, or adhesive) in such a manner that wires of one layer are aligned relative to wires one another layer.

In another embodiment, the layers are configured such that a part of a braid is aligned with wires of another layer, and a part of a braid is offset with wires of another layer. Similar to the above description, the binding mechanism and pattern can be configured in a particular way in various areas of a braid to accomplish this.

Note, with a spiral shape flow diversion stent as shown in FIG. 9, it is generally beneficial to have individual windings 118a of the spiral pattern directly flush against, or overlapping with (meaning part of a winding is positioned above or below an adjacent winding), an adjacent individual winding 118b. The purpose is that so there are no gaps between the windings that blood can get through to otherwise track into the aneurysm unimpeded. In one embodiment, a directly adjacent or overlapped configuration can be set during the winding pattern over the mandrel (e.g., where the spiral pattern is wound such that adjacent windings are flush against or overlap with each other). In another embodiment, a small gap can be introduced between adjacent windings; however, since a flow diversion stent is typically oversized relative to the vessel it is placed in a treatment procedure (this is generally done to ensure a flow diversion stent will be positioned flush relative to the aneurysm neck), this oversizing will then cause adjacent windings to sit directly adjacent each other or to overlap slightly so that there is no open space between the windings of a stent when implanted.

Figure 11:
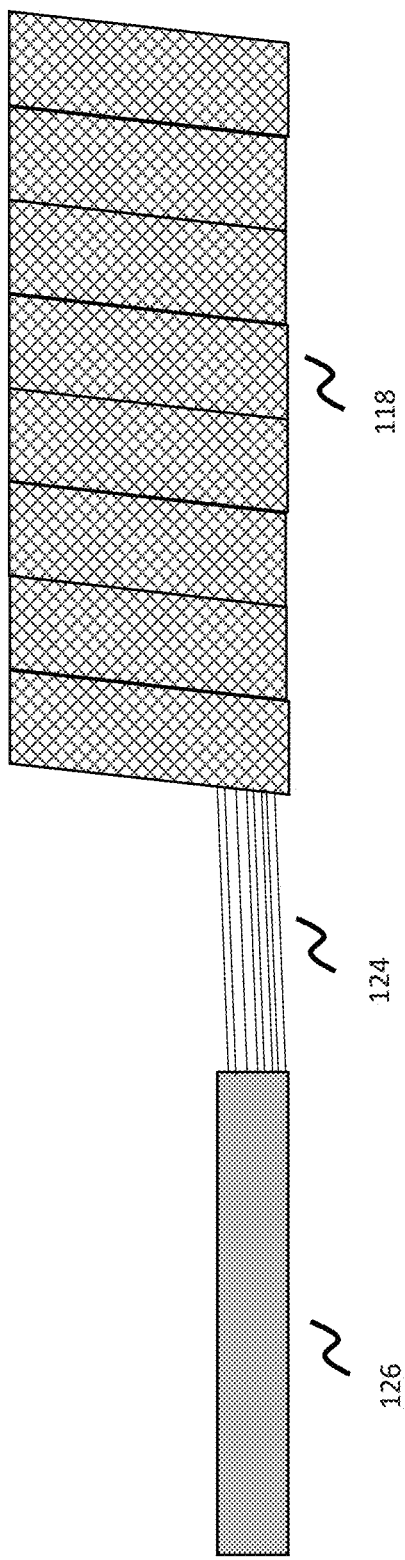
FIG. 11 illustrates a delivery system used to deliver a spiral structure, according to one embodiment.

Stent 118 is connected to a delivery pusher 126 used to deliver stent 118 through a catheter and to the target treatment location, as shown in FIG. 11. Stent 118 adopts a flattened/compressed and elongated configuration when within the delivery catheter, and then an expanded spiraled shape once outside of the delivery catheter.

Note, for the disclosure herein reference will be given to the terms proximal and distal. Proximal should be considered as the direction toward the surgeon conducting the procedure which is also the direction outside of the vasculature, away from the patient. Distal should be considered as the direction toward the patient, which is the direction toward the region of the patient vasculature, or further within the patient vasculature.

Pusher 126 is either a tubular or solid structure, which is gripped at its proximal end by a user and used to push the connected stent 118 through a catheter and to a treatment location. In one embodiment, stent 118 is wound from one or more wires which are wound first in a proximal to distal direction (e.g., left to right in the context of FIG. 11) and then back in a distal to proximal direction (e.g., right to left in the context of FIG. 11). This results in each wire of the one or more wires of the braid being braided in such a manner such that each wire will start at a proximal location and end at a proximal location. The one or more wires forming stent 118 (e.g., 8 wires shown in the exemplar of FIG. 11) are then extended proximally and connected to pusher 126. In this way, stent 118 and pusher 126 are connected via an extended connection interface 124. In one embodiment, wires forming extended connection interface 124 are covered by a tubular covering element, or a covering structure. Though extended wire connection interface 124 is shown as relatively long in the context of FIG. 11, interface 124 can be sized any length and in one example is relatively short so as to minimize the profile of any extension element extending from a proximal end of stent 118. In one embodiment, the connection interface 124 is itself braided such that it is considered a braided extension of the rest of stent 118.

Figure 12:
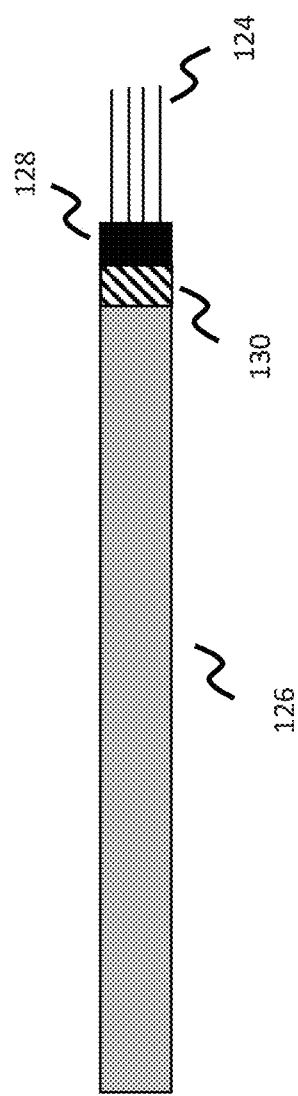
FIG. 12 illustrates a delivery system used to deliver a spiral structure and including a detachment junction, according to one embodiment.

FIG. 12 shows a connection interface 124 between pusher 126 and stent 118 in more detail. Wires forming a proximal end of connection interface 124 are connected to a tubular marker element 128. In one example, marker element 128 is radiopaque to aid in visualization of a distal end of the pusher 126/proximal end of stent 118. In one example, proximal ends of wires forming connection interface 124 are welded or otherwise attached to an internal lumen of the tubular marker element 128 or an external surface of the marker element 128. In an alternative configuration, marker element 128 is a solid structure instead of a tube.

A detachment interface 130 is positioned proximal of the marker element 128. Detachment interface 130 is a detachable junction which is severable (e.g., mechanically, electrolytically, or thermally) in order to detach marker 128 and wire connection interface 124 from the rest of pusher 126. In one embodiment, shown in FIG. 13, detachment interface 130 includes an elongated tether 132 extending between a distal portion of an inner lumen of pusher 126 and marker element 128, and a heater coil 134 connected to pusher 126 and which is capable of being heated based on a user action (e.g., via a proximal button) in order to heat and sever tether 132.

Tether 132, in one example, is attached at one end within an internal lumen of pusher 126 or an external surface of pusher 126, and at another end to an internal lumen of marker element 128. Severing tether 132 will detach marker 128 and the wire interface elements 124 (which are connected to marker 128) from the pusher 126 and heater 134. Heater 134 is not detached and remains connected with pusher 126. Wires (not shown) are connected at each end of heater 134 such that a first wire is connected to a first end of heater 134 and a second wire of an opposing polarity is connected to a second end of heater 134. These wires can run through a lumen of pusher 126 or are external of pusher 126 and run all the way to a proximal end of a pusher, where each wire connects to an associated contact at a proximal end of pusher 126. Each contact is oppositely polarized (one positive, one negative) so that the contacts, wires, and heater form a circuit. The pusher is then connected to an external interface/detachment controller (e.g., a handheld detachment element) to initiate a detachment sequence. The external controller will have appropriate circuitry and a voltage source (e.g., battery) which aligns with the proximally oriented pusher contacts to polarize them and to enable current to flow through pusher 126 (via the wires) to heat the heater 134 to initiate detachment. Further details of thermal detachment systems can be found in U.S. Pat. No. 9,717,500 which is hereby incorporated by reference in its entirety.

Alternative embodiments of a detachment interface 130 can utilize a meltable portion (such as a polymeric junction) heated by a heater to initiate thermal detachment. Other embodiments of a detachment interface 130 can utilize a mechanical connection, such as a screw where a user would simply rotate a screw-like engaging element in a particular direction to initiate detachment. Alternatively, an electrolytic system can be used where one wire is used to polarize a corrodible detachment junction and the patient's blood provides a return current to complete a detachment circuit. Electrolytic detachment systems are discussed in U.S. Pat. No. 5,122,136 which is hereby incorporated by reference in its entirety. Any detachment techniques generally known by one skilled in the art to detach an implant can be used to detach stent 118 from pusher 126.

Although stent 118 has primarily been described as a flow diversion stent, the stent can also serve other functions, for instance as a scaffolding element to prevent other embolic material which occludes an aneurysm (e.g., embolic coils) from migrating out of the aneurysm.

The disclosure up to this point has discussed a spiral shaped element which can be used as a stent, for instance a flow diversion stent. As discussed earlier and herein, a spiral shape is considerably more flexible than a fixed tubular shape (the latter being the traditional stent design and shape). This flexibility has significant advantages in terms of deployment in the smaller blood vessels in the neurovasculature, and across tortuous vasculature where deployment is more difficult and where a stent must have good flexibility to adopt the shape of the vasculature. This flexibility also provides additional advantages that make such a design useful in other medical devices, aside from a stent.

In other embodiments, a spiral structure can be used as an embolic or occlusive element to occlude a target site. A spiral shape has some key advantages in being more flexible, as discussed earlier and herein. This flexibility is also beneficial for occlusive devices, where a flexible device is more capable of manipulation of its shape and adopting the shape of a target region, such as an aneurysm. These characteristics are helpful in occlusion and filling the aneurysm. Furthermore, the augmented filling or occluding characteristics can further provide increased flow disruption at the neck of the aneurysm, thereby helping to prevent blood flow into the aneurysm.

Figure 14:
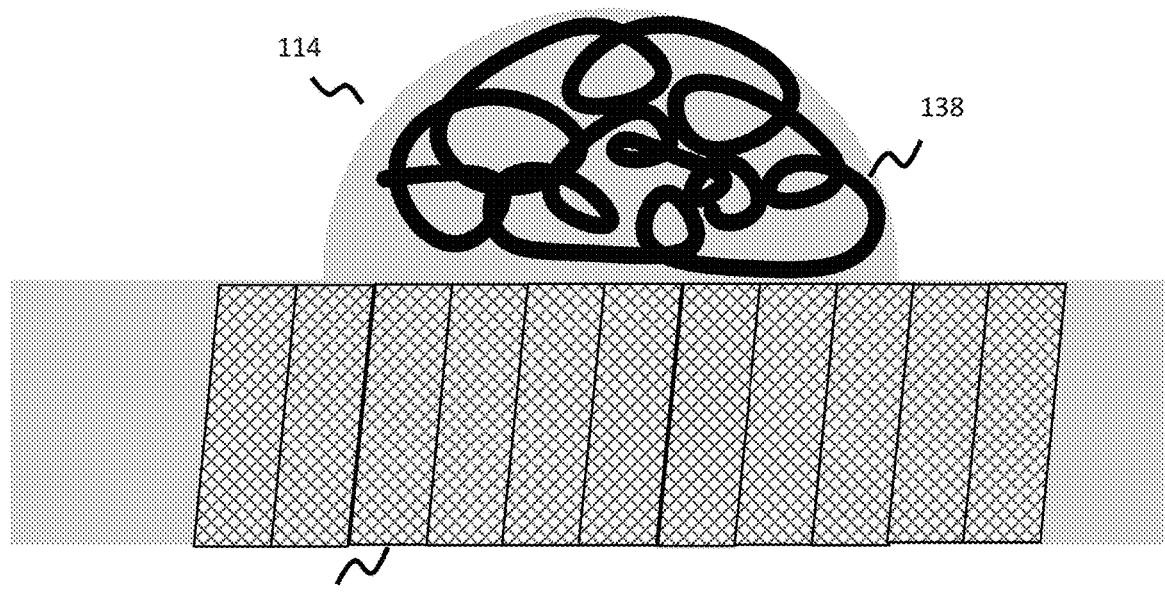
FIG. 14 illustrates a spiral shaped stent treating an aneurysm and a spiral shaped occlusive device to occlude an aneurysm, according to one embodiment.

FIG. 14 illustrates a situation where one or more spiral occlusive structures 138, made in a similar manner to the spiral structures described earlier but configured specifically for occlusive purposes, is deployed into an aneurysm 114. Another spiral stent structure 118 (or alternatively, a traditional tubular stent structure) is positioned against the aneurysm as a scaffolding element to help retain the occlusive structures 138 in the aneurysm.

Occlusive structures 138 when used for an occlusive purpose can be uniquely configured for occlusive purposes (e.g., via sizing of a device, density/pic count of a mesh/braid, and/or wire size used to create a braid/mesh), as opposed to for stenting purpose. Desirable occlusive properties include a small profile and highly flexible shape capable of wrapping within the aneurysm, and spiral occlusive structures 138 can be configured with these parameters to function as an occlusive device. For instance, spiral occlusive structure(s) can be one or more of: smaller, composed of more wires (thereby promoting softness), composed of smaller wires, and/or utilizing a more gapped configuration between the windings—in comparison to a spiral stent 118 structure.

In another embodiment, occlusive structures 138 form other (e.g., non-spiral) shapes. For instance, an occlusive structure can form an elongated linear conformable mesh, where the linear mesh is highly flexible in order to adopt a shape of a target region (e.g., aneurysm). A linear occlusive structure, in one embodiment, includes a wire or elongated element running within an inner passage and between opposing ends of the occlusive structure. An inner wire or elongated element, in one embodiment, is tensioned in order to help deployment and help urge a linear occlusive structure into a curved shape (e.g., to augment a space filling shape) upon deployment.

Figure 15:
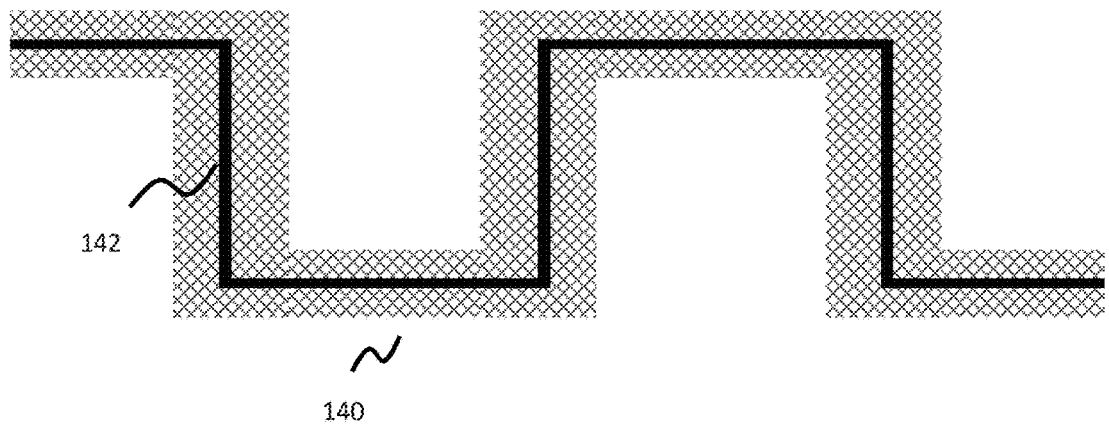
FIG. 15 illustrates an occlusive device with a complex shape and including an internal member, according to one embodiment.

Another embodiment, shown in FIG. 15, utilizes an occlusive structure 140 which has a curvi-linear or complex (e.g., three-dimensional) type of shape. Occlusive structure 140, in one embodiment, is heat set into this complex shape. Alternatively, occlusive structure 140 includes a tensioned internal wire or tether 142 which is heat set into the complex shape that occlusive structure then 140 adopts—such that internal member 142 imparts a force upon occlusive structure 140 to adopt its complex or curvi-linear shape. The shape shown in FIG. 15 is one example of a curvi-linear or complex type shape, but a variety of such shapes can be utilized in order to augment the packing ability and occlusive effect of occlusive structure 140.

Each structure (stent structure 118, and occlusive structure 138, as shown in FIG. 14) is delivered by a separate catheter. A first catheter is deployed into the aneurysm. A second catheter is then deployed in the parent vessel across a neck of an aneurysm and a spiral stent 118 is deployed from the second catheter. One or more spiral occlusive structures 138 (e.g., often for occlusion, a plurality of structures are sequentially deployed until the aneurysm is sufficiently occluded) are then delivered into aneurysm 114 from the first catheter, and the first and second catheters are removed once this procedure is complete.

Medical devices, including stents and occlusive devices, must be sized appropriately relative to a target treatment location. This requires an initial imaging step of the treatment location to determine the appropriate size of a device to treat a target space, so the facility or doctor can then order a device of a specific size to conduct the procedure. However, problems can occur if the target space dimensions are measured incorrectly, or if the device does not properly deploy and thus not properly expand to its intended dimensions in the target space (e.g., due to mechanical issues with the device, or vascular conditions such as tortuous vessels which make deployment or expansion difficult). Furthermore, medical devices are typically configured only to perform their one intended function and cannot be configured to, for example, change shapes to perform another intended function. Additionally, most medical devices are heat set to adopt a particular set deployment shape; however, there is generally not a way to encourage devices to adopt a unique shape based on the particular size or geometry of the particular vascular condition. The following embodiments address at least these issues by utilizing a shape setting system which includes a shape setting structure to help change a shape of a medical device.

Figure 16:
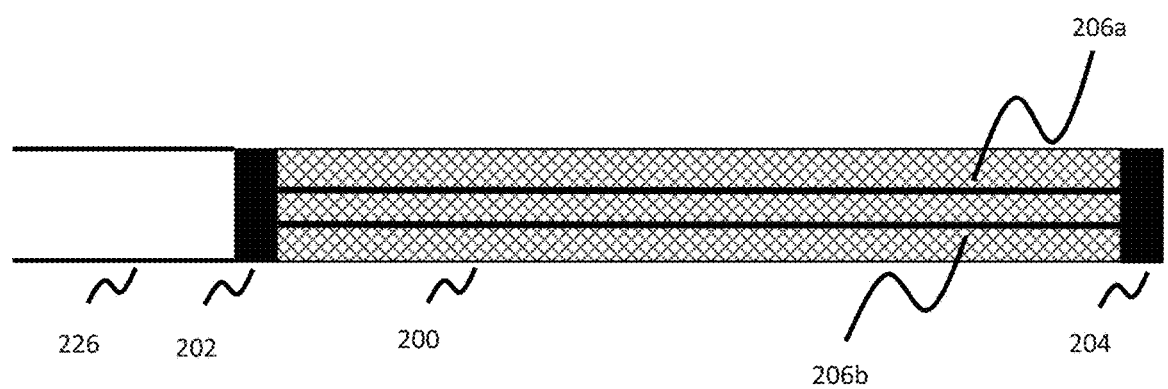
FIG. 16 illustrates an elongated implant including a shape setting structure, according to one embodiment.

FIG. 16 shows an implant 200 composed a braid or mesh of one or more wires. Implant 200 is in a first elongated configuration and is proximally connected to a pusher 226. Implant 200 includes a shape setting structure, which, as will be explained, is used to change a shape, configuration, or profile of braided implant 200. A shape setting structure is part of a larger shape setting system. In one embodiment, a shape setting structure (as shown in FIG. 16) comprises first and second conductive elements 206a, 206b which extend through a length of implant 200.

In one embodiment, conductive elements 206a and 206b are conductive wires which are inter-braided or interwoven with wires of a mesh which comprise implant 200. For terminology, conductive elements 206a, 206b can be considered conductive wire elements, conductive core wire elements, conductive core wire sections, a shape setting member, or a shape setting structure as these function as the elements responsible for shape setting. In one example, conductive elements 206a, 206b are inter-braided or interwoven throughout the mesh in a similar manner to how radiopaque wire 102 was inter-braided through the mesh of FIG. 1, as described earlier herein. In one example, conductive elements 206a, 206b are interwoven of inter-braided through implant 200 in a separate procedure after implant 200 is initially braided with its component wires. In another example, conductive elements 206a, 206b are wound or braided along with constituent wires of the implant braid as implant 200 is braided.

In another embodiment, conductive elements 206a, 206b are directly connected to the braid on either an interior surface or exterior surface of the braid 200, such that conductive elements 206a, 206b directly contact one or more wires of the braid 200 but without being inter-braided or interwoven with implant braid 200.

Shape memory implants (e.g., stents or occlusive devices utilizing shape memory material) typically utilize a first and second shape or configuration, where the first shape/configuration is the shape the implant adopts when restrained within a delivery catheter. This first shape is elongated and compressed, and is considered a stress-induced martensitic phase.

The second shape is imparted with a heat treatment step, where the device is heat treated (e.g. after being wound over a mandrel) at a particular temperature (e.g., about 20 degrees Celsius or 68 degrees Fahrenheit), and is meant to impart an expansion shape which the device adopts when released from the delivery catheter. This shape is considered a superelastic shape, and is considered an austenitic phase. The relatively low temperature ensures that the device will expand at an ambient temperature as well as within the body, which is considerably warmer at about 98.6 degrees Fahrenheit.

A shape setting structure (e.g., conductive wires 206a, 206b) serves to impart a third shape on an implant based on heating of the shape setting structure. Conductive wires 206a, 206b are wound over a mandrel to adopt a particular configuration (e.g., the spiral configuration shown in FIG. 17), whereby conductive wires 206a, 206b are then heat treated in this configuration at a particular temperature that is above body temperature to impart this shape once the particular temperature is reached. This temperature can be considered as a transition temperature whereby conductive wires 206a, 206b then adopt their tertiary shape once heated to this transition temperature. In one example, a transition temperature is anywhere between above body temperature (37 degrees Celsius/98.6 degrees Fahrenheit) to 42 degrees Celsius/108 degrees Fahrenheit. In some examples, a value of 38 degrees Celsius, 39 degrees Celsius, or 40 degrees Celsius can be used as a transition temperature. When used in a procedure, a heating element or system is used to heat conductive wires 206a, 206b to a transition temperature in order to impart a third or tertiary shape. Since the rest of implant 200 is connected to conductive wires 206a, 206b (e.g., since said conductive wires are either interwoven/ inter-braided among the wires of implant 200, or since said conductive wires are directly connected to wires of implant 200), as conductive wires 206a, 206b change their shape into a tertiary shape, the rest of implant 200 also adopts this tertiary shape.

Implant 200 and shape setting structure (e.g., conductive wires 206a, 206b) therefore have three shapes. A first elongated/compressed shape when within a delivery catheter, a second shape when released from the delivery catheter based on exposure to ambient temperature/temperature of blood, and a third shape when shape setting structure/ conductive wires 206a, 206b are heated after the implant 200 has adopted its second shape.

In one embodiment, conductive elements 206a, 206b are configured to not exceed a certain temperature threshold (e.g., 42 degrees Celsius). Techniques to ensure a certain temperature (e.g., 42 degrees Celsius) is not exceeded include configuring the system so that a certain current threshold is not exceeded, where the current threshold is associated with a particular temperature (e.g., 42 degrees Celsius) to ensure a certain temperature is never reached or broached. Alternatively, an auto-shutoff feature can be triggered once a certain current or temperature threshold is detected.

In one embodiment, braided implant 200 is configured similar to other multiple (2 or more) layer braids discussed earlier and shown in FIGS. 7-9, where a braided implant initially adopts a linear, elongated profile (e.g., if the spiral shape of FIG. 7 or 9 were elongated/stretched), and then adopts the spiral multi-layer shape of FIG. 7 or 9 once conductive elements 206a, 206b reach their transition temperature and change shape into a spiral configuration—thereby urging the rest of implant braid 200 to also adopt a spiral configuration.

In one embodiment, conductive elements 206a, 206b are inter-braided through the mesh implant in a similar manner to how radiopaque wire 102 was inter-braided or interwoven through the implant in FIG. 1, as discussed earlier herein. In one example, conductive elements 206a, 206b are sized similar to the other wires forming mesh implant 200 (e.g., about 0.025 mm-0.075 mm diameter), or sized larger than the wires forming mesh implant 200 (e.g., about 0.05 mm-0.15 mm diameter).

In one embodiment, conductive elements 206a, 206b are composed of a good shape memory material thereby enabling them to be heat set in an appropriate curved or spiral type shape heated/expansion shape; conductive elements 206a, 206b should also be good conductors of electricity to facilitate current passage and heat generation. In one embodiment, nitinol, which is a good shape memory metallic material is used. Other materials, such as stainless steel or cobalt chromium can be used alternatively. In one embodiment, drawn-filled tubing wires are used utilizing a radiopaque metal core (e.g., platinum, platinum/tungsten alloy, gold or tantalum) and a shape memory metal jacket (e.g., nitinol, stainless steel, or cobalt chromium). Conductive elements 206a, 206b can further include high resistance regions along their length (e.g., bands or coiled/spiral shapes) to facilitate heat generation.

Several techniques can be utilized to maximize heat retention along conductive elements 206a, 206b and prevent tissue damage due to heat exposure. In one embodiment, discussed earlier, a current or temperature threshold or an auto-shutoff feature is utilized to keep a certain current or temperature profile along conductive elements 206a, 206b. In another embodiment, an insulation material (e.g., polymer, or a metal with low conductivity) is used around conductive elements 206a, 206b. In one embodiment, the insulation material is circumferentially around the conductive elements 206a, 206b—for instance as a peripheral hollow tube. In one embodiment, the implant 200 itself is coated with an insulative material (e.g., polymer).

Figure 17:
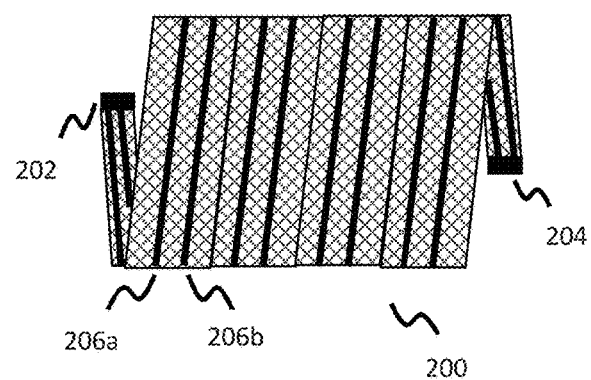
FIG. 17 illustrates the implant from FIG. 16 in a spiral shape, according to one embodiment.

As generally shown in FIG. 17, conductive elements 206a, 206b are connected to a proximal heating mechanism 202. In one embodiment, conductive elements 206a, 206b are composed of one wire which is wound in a first distal direction to a distal end of an implant (thereby forming element 206a) and then wound back in a proximal direction to a proximal end of an implant (thereby forming element 206b). In another embodiment, conductive elements 206a, 206b are two separate wires. A first wire 206a is wound proximally to distally and connects to a conductive band 204. In one embodiment, conductive band 204 is radiopaque (e.g., platinum-iridium, which is radiopaque and also has good conductive properties) to augment visualization of a distal end of the implant and thus function like a radiopaque marker. A second wire 206b is wound distally to proximally and is connected to conductive band 204. Conductive band 204 provides electrical connection between first and second wires 206a, 206b. Alternative configurations can utilize a thin conductive tube instead of a wire to form conductive elements 206a, 206b.

Figure 18:
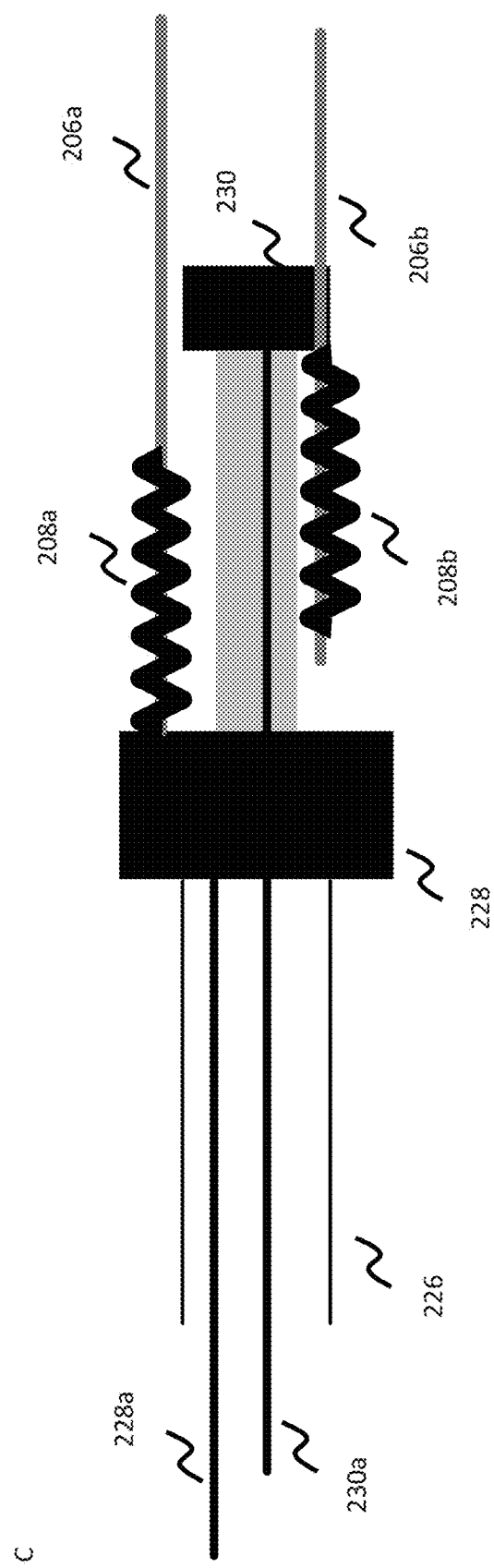
FIG. 18 illustrates an implant/pusher interface for an implant utilizing a shape setting structure, according to one embodiment.

FIG. 18 shows one embodiment of a heating mechanism 202 used to heat conductive elements 206a, 206b. A distal end of pusher 226 includes a first electrical contact 228 and a second electrical contact 230; these are oppositely polarized such that first contact 228, for example, is positive while second contact 230, for example, is negative—though alternatively this configuration can be switched. First and second contacts 228, 230 are polarized via wires 228a, 230a such that wire 228a is connected to contact 228 and wire 230a is connected to contact 230. Wires 228a, 230a are each connected to an oppositely charged voltage source (e.g., positive and negative terminals) at a proximal end of the system, and in this way these wires convey an associated current to each contact 228, 230.

In one embodiment, one or more of contacts 228, 230 are tubular bands; where a tubular configuration allows wire 230a to pass through a more proximally oriented contact 228 to connect to distal contact 230. As shown in FIG. 18, each contact is enlarged relative to a distal section of pusher 226. Proximal ends of conductive elements 206a and 206b are shown in FIG. 18, where FIG. 18 shows how proximal ends of conductive elements 206a, 206b connect to the heater mechanism. Conductive element 206a has a coil 208a at its proximal end; proximal coil 208a is conductive and enables electrical connection with contact 228. Second conductive element 206b has a coil 208b at its proximal end; proximal coil 208b is conductive and enables electrical connection with a second contact 230. In one example, coils 208a, 208b are radiopaque such a tantalum, platinum, palladium, or gold to augment visualization of the proximal end or proximal region of braid implant 200.

Where conductive elements 206a, 206b are composed of one wire with a proximal to distal traversing section (e.g., 206a) and a distal to proximal traversing section (e.g., 206b), then each end of the unitary wire is connected to (or in electrical communication with) a different contact, such that one end connects to contact 228 and the other end connects to contact 230. Where conductive elements 206a, 206b are composed of two separate wires bridged together by a distal conductive band, then a first wire's proximal end connects to contact 228, while a second wire's proximal end would connect to contact 230.

Since a proximal end of first conductive element 206a is connected to a first contact 228 of one polarity (e.g., positive polarity) and a proximal end of second conductive element 206b is connected to a second contact 230 of another polarity (e.g., negative polarity), a circuit is completed whereby current will flow from, for example, first conductive element 206a distally to a distal end of a braided implant and back via second conductive element 206b. The current flow causes first and second conductive elements 206a, 206b to heat up and thereby adopt the spiral or curved shape memory to urge the braided implant into its subsequent (e.g., spiraled) shape.

A user would activate the heating mechanism via a hand-held mechanism containing a power/voltage source (e.g., pressing a button on a handheld controller connected to a proximal end of pusher 226) to cause a current to pass through the contacts and through the connected conductive elements 206a, 206b to cause an implant 200 to adopt a spiral-like shape, profile, or configuration.

The embodiment presented in FIG. 18 would not necessarily need a detachment system to detach implant 200 from pusher 226 since when braided implant 200 (or at least a proximal end of implant 200) is contained within a delivery catheter, proximal marker coils 208a, 208b which form proximal ends of conductive elements 206a, 206b are contained within a recess defined between enlarged contacts 228, 230—this is shown in more detail in FIG. 19 in the context of an overlying delivery catheter 232. Marker coils 208a, 208b are horizontally constrained between enlarged contacts 228, 230 and vertically constrained by the overlying introducer sheath/catheter 232 and the underlying pusher section.

When an entire implant 200 is pushed distally or catheter 232 is retracted to fully expose implant 200, marker coils 208a, 208b are no longer restrained, which then releases the implant—as shown in FIG. 20. The rest of the wires forming implant 200, in one embodiment, are connected to a distal band element (not shown, but positioned distally of contact 230). The band element can function similar to marker 128 of FIG. 12 which acts as a proximal gathering location for the wires forming an implant 200. This additional band element is part of the implant itself and therefore detaches along with the implant—while contact 230 and everything proximal of the contact is part of or connected to the pusher 226 and therefore is not detached along with implant 200.

Figure 13:
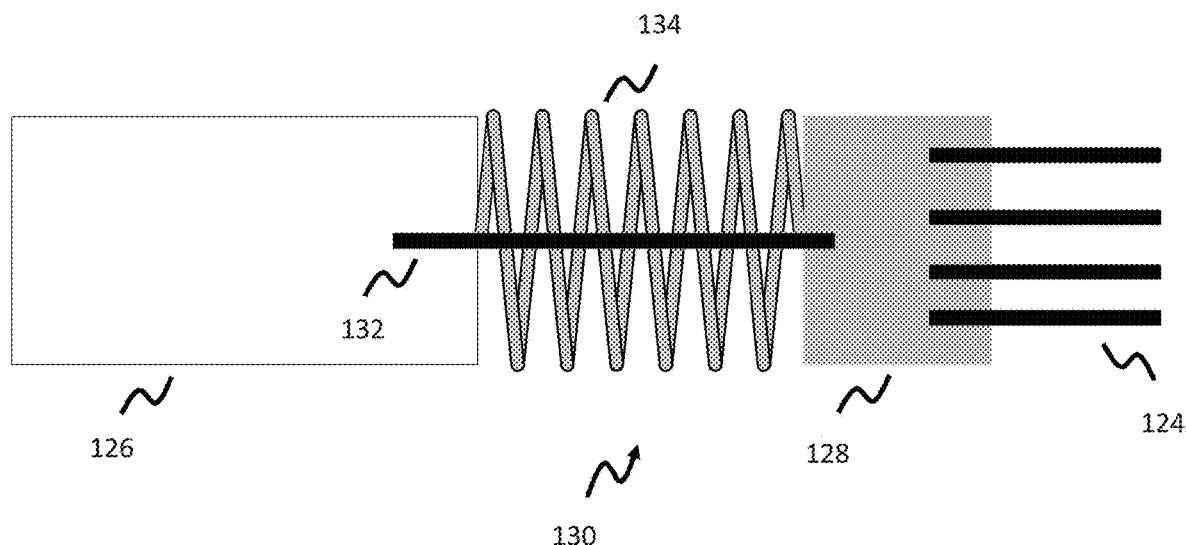
FIG. 13 illustrates a heating element used to detach a spiral structure, according to one embodiment.

In an alternative embodiment, rather than catheter 232 providing a restraining force to prevent or enable detachment, a detachment system (e.g., an electrolytic, mechanical, or thermoelectric system) such as the one shown in FIG. 13 is used, whereby the user can interact with a controller mechanism connected to a pusher 126, 226. The controller mechanism would have two control interfaces (e.g., buttons) where activating a first button would heat the conductive elements 206a, 206b to cause the implant to adopt a spiral-like post-expansion shape, and activating a second button would activate a detachment system to then detach the implant.

One major advantage of the use of a shape setting structure (e.g., conductive elements 206a, 206b) in helping an implant 200 adopt a subsequent post-deployment shape is that a device does not necessarily need to be sized specifically to be used in a vasculature setting (e.g., as a flow diversion stent or as an occlusive device). Even if a diameter of a spiral shape is larger than the blood vessel the device is placed into, the walls of the vessel provide a retention force to limit how large a shape the device can adopt. Therefore, in one example, a one size fits all elongated structure can be used to treat a variety of vessel sizes and vasculature conditions—where the elongated structure then adopts a different shape (e.g., a spiral-like shape) after a shape setting structure is heated/activated.

The systems and methods used to apply current through conductive elements 206a, 206b of an implant to cause it to adopt another shape can be used in a variety of different ways, aside from causing an implant to adopt a spiral shape. For instance, this technique and system can be used to cause an implant to adopt a wide variety of distinct, different shapes (e.g., not only a spiral shape). The key feature is that conductive elements 206a, 206b are wound into a particular shape and then thermally heat set at a specific transition temperature so that conductive elements 206a, 206b then adopt this shape once heated to this specific transition temperature. The rest of the implant then adopts the shape of the conductive elements once this specific transition temperature is reached by nature of being connected to or inter-braided with conductive elements 206a, 206b.

In one embodiment, the shape parameters are reversed such that the initial primary or delivered shape (e.g., the expanded shape the device initially takes on when delivered out of a delivery catheter) is a spiral or coil-like shape, and then the subsequent or tertiary shape that the conductive elements 206a, 206b (and implant 200) adopt once heated is a more elongated or linear shape.

Figure 22:
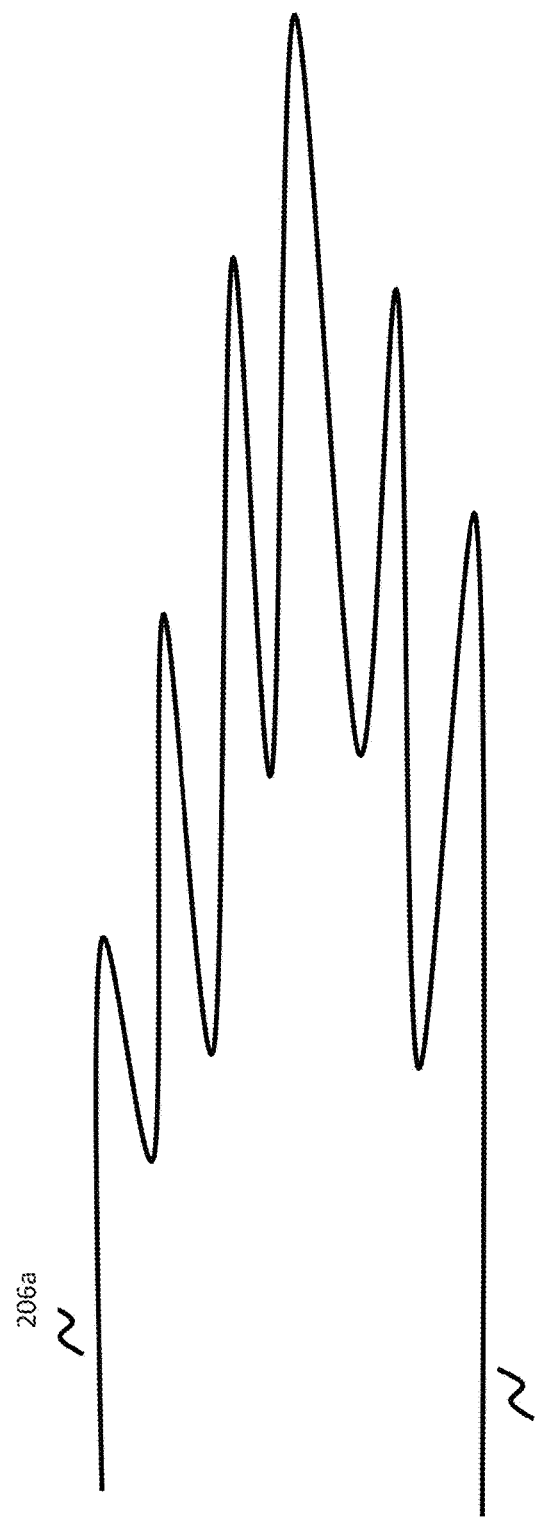
FIG. 22 illustrates a shape setting structure with a tortuous shape, according to one embodiment.

In alternative embodiments, conductive elements 206a, 206b can have alternative configurations other than the one or two elements illustratively shown in FIGS. 16-17. In the context of FIG. 18, conductive elements 206a, 206b have two proximal end sections that enable connection with pusher 226 and electrical connection with the polarized contacts 228, 230. However, conductive elements 206a, 206b can have a complex shape that proximally culminate into two proximal nodes or extensions. For instance, instead of an elongated wire section proceeding from a proximal end to a distal end of the implant and back again proximally, an elongated wire section can proceed tortuously (e.g., with a number of curves or complex shapes)—an example of which is shown in FIG. 22. One advantage of this configuration is that a larger area of implant braid 200 will contact regions of conductive elements 206a, 206b, thereby augmenting a shape manipulation effect to the implant braid 200 when the conductive elements adopt their particular shape profile once heated to the particular transition temperature. In another configuration, conductive elements 206a, 206b can utilize more of a scaffolding shape similar in structure to the implant braid 200 but positioned over, under, or interwoven with the implant braid 200—one advantage of this configuration is that many sections of the implant braid 200 will have an immediately adjacent conductive element 206a, 206b thereby augmenting a shape manipulation effect to the implant braid 200 when conductive elements 206a, 206b adopt their tertiary shape once heated to the particular transition temperature. Even though selective shapes are illustratively shown or described to provide examples, any number of shapes are contemplated without restriction since any shape can be created just by utilizing a particular wind shape for the shape setting member (e.g., conductive elements 206a, 206b). For instance, FIG. 15 shows an alternatively complex shape that can be utilized as a tertiary shape that can be selectively activated through activation of a shape setting member.

Figure 21:
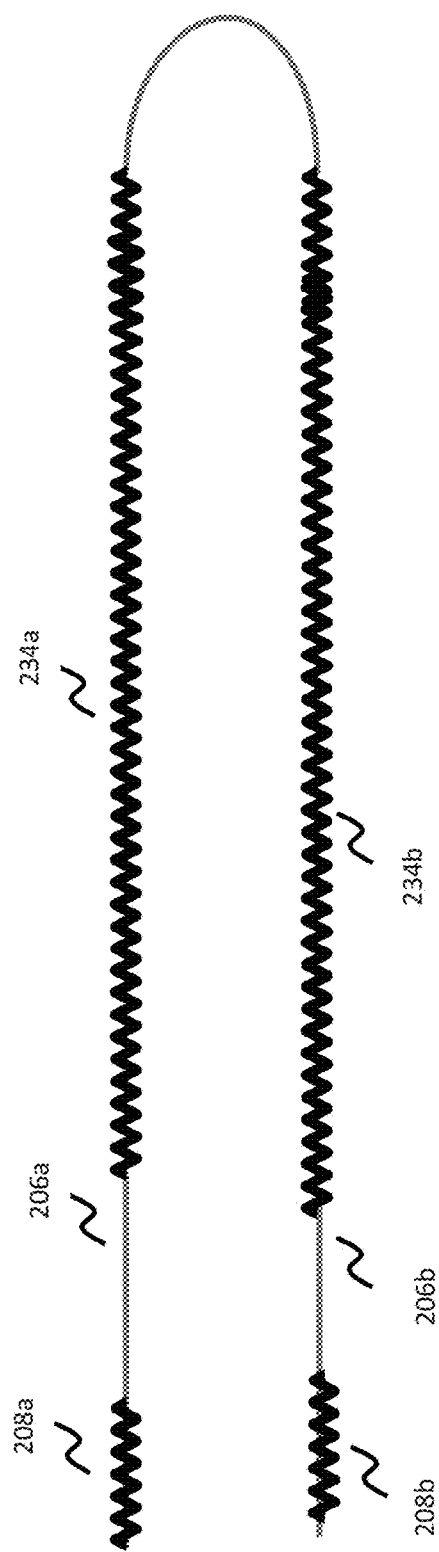
FIG. 21 illustrates a shape setting structure with coil-like shapes along a portion of its length, according to one embodiment.

In one embodiment, shown in FIG. 21, conductive elements 206a, 206b include a medial spring-like or coil-like shape 234a, 234b. One advantage to this shape is that the nested windings of these shapes increase resistance as current flows through these sections, thereby increasing associated temperature and therefore allowing conductive elements 206a, 206b to increase in temperature without necessarily utilizing much current flow. Though this configuration is shown as utilizing one consistent shape (meaning conductive elements 206a, 206b are one unitary element), this configuration can alternatively utilize a connective band (e.g., band 204 of FIG. 16) and two separate wire elements in electrical communication via the connective band.

The shape setting structure discussed herein can be used such that an implant selectively adopts a particular shape or configuration when heated to a particular transition temperature point after deployment. In some embodiments, the mechanism can be used to selectively allow the implant to either operate as an occlusive device or as a stent device, wherein the device in a first elongated and deployed configuration can act as an occlusive mesh, but the user has the option to have the implant adopt a different spiral-like configuration to act as a flow diverter. In some embodiments, the mechanism can be used to selectively allow the implant to adopt multiple shapes to treat a particular condition. For instance, a user can treat an aneurysm with an elongated braid, or activate a different, subsequent shape configuration via activation at a transition temperature to cause the braid to adopt another (e.g., spiral) configuration to then occlude the aneurysm with this alternate spiral shape.

In one example, a plurality of implants 200 capable of selectively adopting a tertiary (e.g., spiral) shape can be used for a plurality of purposes in a treatment location. For instance, a user can first deploy a first implant across the neck of an aneurysm in the adjoining vessel as a stent where a particular shape (e.g., spiral) is activated through the shape setting member. The user can then deploy a second implant as an occlusive member in the aneurysm where the user can optionally activate a shape setting member to have the implant adopt a particular (e.g., spiral) shape to take on another occlusive shape.

In alternative embodiments, the heating system (via contacts 228, 230 which are configured to convey current through shape setting member/conductive elements 206a, 206b) is configured with a user interface such that the user can apply a selective amount of current to control the degree to which the shape setting members/conductive elements 206a, 206b adopt their tertiary (e.g., spiral) shape—thereby controlling the degree to which the implant 200 adopts its own tertiary (e.g., spiral) shape. In this way, the user can control the degree to which the implant changes its shape. As conductive elements 206a, 206b reach their shape memory transition temperature, they will start to adopt a particular (e.g., spiral) shape. In one embodiment, this may not necessarily be an immediate transition as continued exposure to current at the transition point will cause an associated shape-change over time. In one example, a user can activate a dial or button to start a shape transition process and then stop the transition via activation of the same dial or button (e.g., moving a dial up and then down, or toggling a button once and then toggling it off by pressing it again) once a certain desirable shape is reached (e.g., a partial spiral instead of a fully spiral shape). In this way, a user has control over the particular final shape profile of an implant. This control is desirable in certain circumstances, for instance where an implant is oversized compared to a vessel and a partial-spiral shape will fit the target therapeutic area, for instance, to act as a flow diverter. Alternatively, if a user wanted to use the implant as an occlusive device, the user can control the final deployment shape of the occlusive device based on the particular geometry or shape of the target therapeutic area (e.g., aneurysm). In alternative embodiments, the heat-induced/current-induced shape formation is more immediate; non-exhaustive factors influencing the time consideration include: the size of an implant, how much of an implant is in contact with the shape setting structure, power associated with a heating system and how much current is passing through a shape setting structure (e.g., conductive elements 206a, 206b), and the difference between body temperature and the shape memory transition temperature of the shape setting structure.

Please note, the embodiments with respect to FIGS. 16-22 have generally utilized a three phase shape mechanism, where a first elongated/compressed shape is adopted in a delivery catheter, a second expanded shape is adopted when freed from the delivery catheter and a particular low ambient temperature is reached, and a third post-expansion shape is adopted when a shape setting member or structure is subsequently heated to a particular transition temperature. In some terminologies, the shape an implant adopts when within a catheter can be considered a first or delivery shape, the shape an implant adopts when initially expanded upon being freed from the catheter can be considered a secondary shape, and the shape an implant adopts (e.g., spiral) when a shape setting structure is heated to a particular transition temperature can be considered a tertiary shape. Alternatively, the stent can be thought of as taking on a first or primary expansion shape upon being released from the delivery catheter, and then a secondary expansion shape after the shape setting structure is heated to a particular transition temperature to impart a different post-deployment shape (e.g., spiral) onto the implant.

In terms of terminology, an implant according to embodiments herein can comprise three shapes, or three states when utilized with the shape setting structure disclosed herein (the structure can also be considered a state setting structure as it affects the shape and/or state of an implant). An implant is in a first compressed or elongated state occurs when contained within a delivery catheter. An implant is in a second resting or expansion state, which the implant adopts once released from the delivery catheter and exposed to ambient or blood temperature thereby causing the implant to adopt its expanded delivery configuration. Finally, an implant is in its third or final state when heating is applied to the implant after delivery (e.g., via heating of the shape or state setting structure, as described in the various embodiments above and herein)—this third or final state can be considered a post-expansion state or a final-pre set state. The final-pre set state can be considered an operative state or operative shape, as the operation or procedure will utilize this third or final state.

Though the description has primarily illustrative described the use of a shape or state-setting structure in conjunction with an implant configured as a stent or occlusive device, this structure can be used in principal to change a shape or state of a variety of implants, and as such these embodiments are not limited in any way. Though the term stent is often used in the specification, the embodiments described herein can be used on a variety of vascular-prosthesis devices, such as stents, stent-grafts, and vascular scaffolds.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implant for treating an aneurysm comprising:
   a scaffold structure comprising one or more scaffold wires braided together to form an elongated flattened mesh; and,
   one or more conductive wires positioned along the elongated flattened mesh;
   wherein the one or more conductive wires have a transition temperature above body temperature such that below the transition temperature the elongated flattened mesh is in a linear, ribbon configuration and such that above the transition temperature the one or more conductive wires maintain the elongated flattened mesh in a spiral configuration; and,
   wherein the one or more conductive wires further comprises a first conductive wire and a second conductive wire connected by a distal conductive band.

2. The implant of claim 1, wherein the one or more conductive wires are directly connected to the elongated flattened mesh on either an interior surface of the elongated flattened mesh or an exterior surface of the elongated flattened mesh, such that the one or more conductive wires directly contact the elongated flattened mesh without being inter-braided or interwoven with the elongated flattened mesh.

3. The implant of claim 1, wherein the one or more conductive wires are interwoven with the elongated flattened mesh.

4. The implant of claim 1, wherein the elongated flattened mesh is formed from a flattened braided tube.

5. The implant of claim 1, wherein the one or more conductive wires have a medial coil shape.

6. The implant of claim 1, further comprising a first conductive coil disposed around the one or more conductive wires.

7. The implant of claim 1, wherein the one or more conductive wires are coated with an insulation material.

8. The implant of claim 1, wherein the implant is connected to a delivery system that includes a predetermined temperature limit above which a temperature of the one or more conductive wires are not increased.

9. The implant of claim 8, wherein the delivery system further comprises an auto-shutoff feature triggered when the one or more conductive wires reach the predetermined temperature limit.

10. The implant of claim 1, wherein the implant is connected to a delivery system that includes a predetermined current threshold that is associated with a predetermined temperature.

11. An implant for treating an aneurysm comprising:
    a scaffold structure comprising one or more scaffold wires braided together to form an elongated flattened mesh; and,
    one or more conductive wires positioned along the elongated flattened mesh;
    wherein the one or more conductive wires have a transition temperature above body temperature such that below the transition temperature the elongated flattened mesh is in a linear, ribbon configuration and such that above the transition temperature the one or more conductive wires maintain the elongated flattened mesh in a spiral configuration;
    wherein the one or more conductive wires further comprise a first conductive wire and a second conductive wire; and wherein a first conductive coil is disposed around a proximal portion of the first conductive wire and a second conductive coil is disposed around a proximal portion of the second conductive wire.

12. The implant of claim 11, wherein the first conductive wire contacts a first electrical contact within a delivery device and the second conductive coil contacts a second electrical contact within a delivery device.

13. The implant of claim 12, wherein the delivery device includes a recess between the first electrical contact and the second electrical contact;
    and wherein the first conductive coil and the second conductive coil are horizontally constrained within the recess.

14. A medical implant comprising:
   an elongated flattened mesh means for forming a body of the implant; and,
   one or more conductive element means for changing a shape of the elongated flattened mesh, the one or more conductive element means extending between a proximal portion and a distal portion of the elongated flattened mesh;
   wherein the one or more conductive element means have a transition temperature above body temperature such that below the transition temperature the one or more conductive element means and the elongated flattened mesh means are in a linear, ribbon configuration and such that above the transition temperature the one or more conductive element means transitions the elongated mesh to a spiral tubular shape; and,
   wherein the one or more conductive element means comprise a first conductive wire and a second conductive wire connected by a distal conductive band.

15. The medical implant of claim 14, wherein the one or more conductive element means have a medial coiled shape.

16. The medical implant of claim 14, further comprising a first conductive coil disposed around the one or more conductive element means.

17. A method of changing a shape of an implantable device comprising:
   advancing a delivery device with a scaffold structure within a patient, the scaffold structure comprising an elongated flattened mesh and being advanced in a linear, ribbon configuration;
   at least partially releasing the scaffold structure from the delivery device;
   providing heat through one or more conductive wires positioned along the elongated flattened mesh until the one or more conductive wires are above body temperature and exceed a transition temperature;
   wherein exceeding the transition temperature changes a shape of the elongated flattened mesh to a spiral shape;
   wherein the at least partially releasing the scaffold structure from the delivery device further comprises releasing at least a first conductive coil connected to the one or more conductive wires from a recess of the delivery device; wherein the recess comprises an electrical contact.

* * * * *